United States Patent [19]

Jensen et al.

[11] Patent Number: 6,069,265
[45] Date of Patent: May 30, 2000

[54] PROCESS FOR THE SYNTHESIS OF 1-AZA-5-HALO-5-STANNABICYCLO[3.3.3] UNDECANE CARBAPENEM INTERMEDIATES

[75] Inventors: Mark S. Jensen, Holmdel; Chunhua Yang, Edison; Nobuyoshi Yasuda, Mountainside; David A. Colon, Plainsboro; Yi Xiao, Fanwood, all of N.J.

[73] Assignee: Merck & Co., Inc., Rahway, N.J.

[21] Appl. No.: 09/377,391

[22] Filed: Aug. 19, 1999

Related U.S. Application Data

[60] Provisional application No. 60/100,319, Sep. 15, 1998.

[51] Int. Cl.$^7$ ...................................................... C07F 7/22
[52] U.S. Cl. ................................................................ 556/87
[58] Field of Search ......................................... 556/87, 81

[56] References Cited

U.S. PATENT DOCUMENTS 5,756,725  5/1998  Wilkening et al. ...................... 540/302

OTHER PUBLICATIONS

Organometallics by Ute et al 14(6), pp 2827–2834, Jun. 1995.

K. Jurkschat et al. *J Organometallic Chemistry*, pp 272 C13–C16 (1984).

K. Jurkschat et al., *Z Anorg. Allg. Chem.*, 560, pp 110–118 (1983).

E. Vedejs et al., *J. Amer. Chem. Soc.*, 114, pp 6556–6558, (1992).

M. Lautens et al., *Agnew Chem. Int. ed. Engl.*, 35, pp 1329–1330 (1996).

*Primary Examiner*—Johann Richter
*Assistant Examiner*—Jean F Vollano
*Attorney, Agent, or Firm*—Sylvia A. Ayler; Mark R. Daniel

[57] ABSTRACT

The present invention relates to a process for synthesizing novel intermediates of formula III:

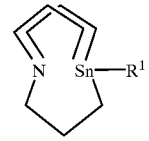

III wherein $R^1$ is a halogen. The intermediate compounds described herein are useful for the preparation of carbapenem compounds.

34 Claims, No Drawings

PROCESS FOR THE SYNTHESIS OF 1-AZA-5-HALO-5-STANNABICYCLO[3.3.3] UNDECANE CARBAPENEM INTERMEDIATES

This application claims the benefit of provisional application Ser. No. 60/100,319, filed Sep. 15, 1998.

BACKGROUND OF THE INVENTION

The present invention relates to a process for synthesizing 1-aza-5-halo-5-stannabicyclo[3.3.3]undecane, which can be used for making compounds such as carbapenems.

Many of the carbapenems are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). These antibacterials thus comprise an important contribution to therapy for treating infections caused by these difficult to control pathogens. There is an increasing need for agents effective against such pathogens (MRSA/MRCNS) which are at the same time relatively free from undesirable side effects.

Previously reported synthesis of 1-aza-5-chloro-5-stannabicyclo[3.3.3]undecane proceeded in low yields, used highly toxic or expensive reagents and were impractical for large scale synthesis. See Jurkschat, K., et al., *J Organometallic Chemistry*, 272, C13–C16 (1984); Jurkschat, K., et al., *Z. Anorg Allg. Chem.* 560, 110–118 (1983); Vedejs, E. et al., *J Amer. Chem. Soc.* 114, 6556–6558, (1992); Haight, A., *University of Wisconsin-Madison, Thesis for PH.D.*, entitled Intramolecular Activation of Tin-Hydrogen and Tin-Carbon Bonds, 1–216 (1990) and Lautens, M, et al., *Agnew Chem. Int. ed. Engl.*, 35, 1329–1330 (1996).

The invention disclosed herein provides a reliable process for economically synthesizing 1-aza-5-halo-5-stannabicyclo[3.3.3]undecane intermediates.

SUMMARY OF THE INVENTION

In one aspect of the invention, a process of synthesizing a 1-aza-5-halo-5-stannabicyclo[3.3.3]undecane intermediate of formula III

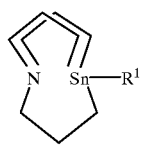

III is described wherein $R^1$ represents a halogen, comprising:
treating a compound of formula II:

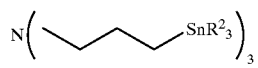

II wherein $R^2$ is alkyl or aryl;
with a tin halide ($SnR^1_4$) wherein $R^1$ is as defined above;
in the presence or absence of a solvent, at temperatures of from about room temperature to about 200° C. to produce a compound of formula III.

DETAILED DESCRIPTION OF THE INVENTION

The invention is described herein in detail using the terms defined below unless otherwise specified.

The term "halogen or halo" is intended to include the halogen atoms chlorine, bromine, fluorine and iodine.

The term tin halide is intended to include $SnCl_4$, $SnBr_4$, $SnI_4$, $SnF_4$, $SnCl_2$, $SnBr_2$, $SnI_2$ and $SnF_2$.

The term stannylating agent is intended to include trialkyltin anions, triaryltin anions, trialkyltin hydrides and triaryltin hydrides.

Aryl refers to 6–10 membered aromatic rings e.g., phenyl, substituted phenyl, and the like, as well as rings which are fused, e.g., naphthyl, phenanthrenyl and the like. An aryl group thus contains at least one ring having at least six atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryl groups include phenyl and naphthyl.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl.

Examples of suitable $R^1$ groups are chlorine, bromine, iodine and fluorine. Preferred $R^1$ groups are chlorine, bromine or iodine.

Examples of suitable $R^2$ groups are $C_{1-10}$ alkyls or aryl groups such as phenyl and naphthyl. Preferred $R^2$ groups are methyl, ethyl, propyl, butyl and phenyl.

1-Aza-5-chloro-5-stannabicyclo[3.3.3]undecane is useful in preparing carbapenem compounds such as those disclosed in U.S. Pat. No. 5,756,725, which is hereby incorporated by reference.

In another aspect of the invention herein, a process of synthesizing a compound of formula III comprising:

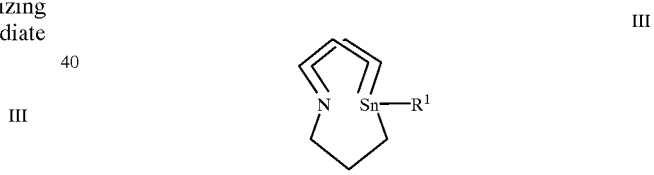

III stannylating a compound of formula I:

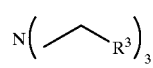

I wherein $R^3$ is a vinyl group or $CH_2CH_2X$ and X is a halogen, O-mesylate, O-tosylate or O-triflate;
with a stannylating agent to produce a compound of formula II:

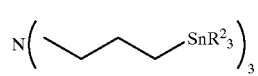

II wherein $R^2$ is alkyl or aryl;
treating the compound of formula II in the presence of a proton source with a tin halide in the presence or absence of a solvent and at temperatures of from about room temperature to about 200° C. to produce a compound of formula III.

For purposes of this invention a suitable tin halide is $SnCl_4$, $SnBr_4$ or $SnI_4$.

A suitable stannylating agent is $Bu_3SnLi$, $Bu_3SnK$, $Bu_3SnMgX$ or $Bu_3SnH$. When $Bu_3SnMgX$, $Bu_3SnLi$, or $Bu_3SnK$, is employed it is preferable that $R^3$ is $CH_2CH_2X$. Likewise, when $Bu_3SnH$ is used $R^3$=vinyl is preferred.

The reaction is generally carried out in the presence or absence of a solvent. When a solvent is employed it can generally be a hyrocarbon such as xylene, toluene, hexane, heptane and the like.

Suitable proton sources are commonly known in the art and are used in the reaction as a promoter. Examples of promoters are $C_{1-6}$ alcohol, water and the like. Examples of alcohols are ethanol, methanol, butanol, propanol, isopropanol, and the like. When water is used as the promoter the ratio of water to tin halide is from about 0.10 to about 2.0 (mol/mol). Likewise, when an alcohol is used as the promoter the ratio of alcohol to tin halide is from about 0.25 to about 1.0 (mol/mol).

The reaction is carried out at a temperature of about room temperature to about 200° C., preferably at about 50° C. to about 150° C.

A preferred aspect of the invention is realized when $R^3$ is $CH_2CH_2X$ and X is chloride, the stannylating agent is $Bu_3SnLi$ and the tin halide is $SnCl_4$.

The process of the present invention is illustrated by the following non-limiting generic scheme:

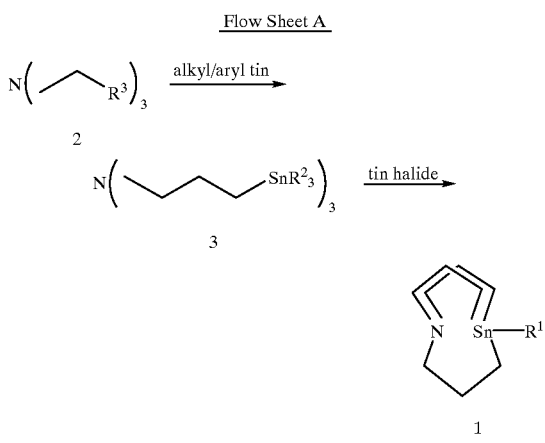

The stannane (3) was prepared in two ways. In the case of $R^3=CH_2CH_2Cl$; prepared by the method described in J. Am. Chem. Soc., 1992, 114, 8138–8146, reaction with $Bu_3SnLi$ provides the stannane (3). In the case of R3=vinyl, reaction with $Bu_3SnH$ gave the stannane (3).

The 1-aza-5-halo-5-stannabicyclo[3.3.3]undecane is prepared as illustrated in Flow Chart A. Treatment of stannane (3) with a tin halide such as $SnCl_4$ is carried out under nitrogen atmosphere in the absence of a solvent or in the presence of a suitable solvent such as toluene, xylene, hexane, or heptane to give the desired compound (1). The reaction is performed at a temperature of about room temperature to about 200° C. for a period of about 1 to about 24 hours. It is preferred that the synthesis reaction is carried out at temperatures of about 75° C. to about 100° C. for a period of about 3 hours in the presence of a proton source. The reaction mixture of the 1-aza-5-halo-5-stannabicyclo[3.3.3] undecane (1) is purified and isolated as crystals.

The intermediates of the instant invention are useful for making compounds such as carbapenems, disclosed in U.S. Pat. No. 5,756,725, which are valuable as antibacterial agents that are active against various Gram-positive and to a lesser extent Gram-negative bacteria, and accordingly find utility in human and veterinary medicine.

Many of the compounds that can be made in accordance with the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier.

The invention is further described in connection with the following non-limiting examples.

PREPARATIVE EXAMPLE 1

Preparation of Tris[3-(tributyltin)propyl]amine from Tri(3-chloropropyl)amine

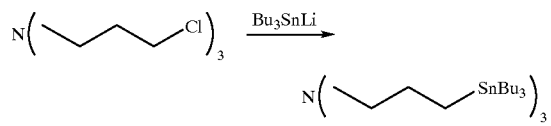

Tributyltin hydride (122 mL) was added dropwise over 1.5 h to a solution of lithium diisopropylamide (2 M in heptane/THF/ethylbenzene, 213 mL) and tetrahydrofuran (THF) (80 mL) at −2° C. to 5° C. After 1 hour at 5° C., a solution of tri(3-chloropropyl)amine (25 g) and THF (100 mL) was added over 30 minutes. After 12 hours at room temperature, the mixture was partitioned between t-BuOMe (200 mL) and saturated aqueous $NH_4Cl$ (200 mL). The organic layer was washed with saturated aqueous $NH_4Cl$ (2×200 mL) and then water (200 mL). The organic layer was dried over $Na_2SO_4$ and concentrated. The resulting light brown oil (148 g, 54 wt %, 79% yield) was used without further purification. An analytical sample was prepared by chromatography on silica eluting with hexanes followed by 10% ethyl acetate/hexanes.

$^1$H NMR (250 MHz; $CDCl_3$):δ2.37 (dd, J=7.7 Hz, 6H), 1.62 (m, 6H), 1.47 (m, 18H), 1.30 (m, 18H), 0.78–0.94 (m, 45H), 0.71 (dd, J=8.3 Hz, 6H)

$^{13}$C NMR (100 MHz; $CDCl_3$):δ59.0, 29.1, 27.5, 24.4, 13.6, 8.7, 6.2.

PREPARATIVE EXAMPLE 2

Preparation of Tris[3-(tributyltin)propyl]amine from Triallylamine

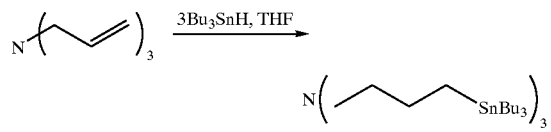

A solution of tributyltin hydride (30 mL) and THF (70 mL) was added over 6 hours to a mixture of triallylamine (3.4 mL), THF (20 mL), and 5% Pd on alumina (122 mg) at room temperature under an atmosphere of nitrogen. After complete addition, the catalyst was removed by filteration through Solka Floc and the solvent was removed in vacuo. The resulting oil was purified by silica gel chromatography by elution with hexanes then 10% ethyl acetate/hexanes to provide 15.60g (66%) of the title compound as a clear colorless oil.

EXAMPLE 1

Preparation of 1-Aza-5-chloro-5-stannabicyclo [3.3.3]undecane

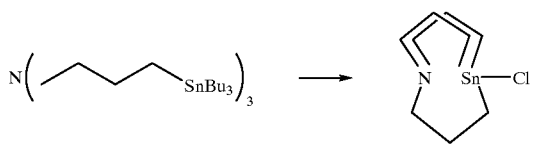

To crude tris[3-(tributyltin)propyl]amine (463 g, 54 wt %, KF=7000 μ/mL) was added SnCl$_4$ (60 mL) at 20 -C under argon. The mixture was warmed to 95 -C to 105 -C for 4 hours. The mixture was cooled to 20 -C, and diluted with acetonitrile (500 mL) and water (25 ml). After 20 hours, the solids were removed by filteration and the acetonitrile solution was extracted with hexanes (5×600 mL). The acetonitrile layer was concentrated in vacuo until solids began to come out of solution. Slow addition of two volumes of ethyl acetate followed by filteration gave 24.5 g (96.2 wt %) of (1) ($R^1$=Cl) as all off-white solid. A second crop (12.3 g, 98.9 wt %) was obtained from the mother liquor. The hexane extracts were concentrated to provide an additional 4.8 g (99.9 wt %). The total yield was 55.8%.

EXAMPLE 2

Preparation of 1-Aza-5-chloro-5-stannabicyclo [3.3.3]undecane

To crude tris[3-(tributyltin)propyl]amine from hydrostannation (12.0g, 88% wt, KF=50 μg/mL) was added SnCl$_4$ (1.8 mL) and water (60 μL) at 70-C. The mixture was warmed to 95 -C for 4 hours. The mixture was cooled to 20 –C, and 10N NaOH (30 mL) was added slowly to keep the temperature about 40–C. The mixture was aged 40 minutes at 40–C. Organic layer was cut and aqueous layer was washed with t-BuOMe (30 mL). Aqueous layer pH was adjustsed to 2.5 with concentrated HCl at 0–C, then extracted with dichloromethane (50 mL). Organic layer was concentrated to afford (1) ($R^1$=Cl) as off-white crystals(1.66g, 53%).

What is claimed is:

1. A process of synthesizing a compound of formula III:

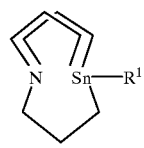

III wherein $R^1$ represents a halogen, comprising:
  treating a compound of formula II:

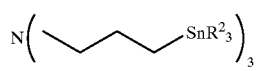

II wherein $R^2$ is alkyl or aryl;

with a tin halide of the formula SnR$^1_4$ wherein $R^1$ is as defined above;
  in the presence or absence of a solvent, at temperatures of from about room temperature to about 200° C. to produce a compound of formula III.

2. A process of synthesizing a compound of formula III in accordance with claim 1 wherein $R^1$ is chlorine, bromine, fluorine or iodine.

3. A process of synthesizing a compound of formula III in accordance with claim 2 wherein $R^1$ is chlorine.

4. A process of synthesizing a compound of formula III in accordance with claim 1 wherein $R^2$ is methyl, ethyl, propyl, butyl or phenyl.

5. A process of synthesizing a compound of formula III in accordance with claim 4 wherein $R^2$ is methyl, ethyl, propyl, or butyl.

6. A process of synthesizing a compound of formula III in accordance with claim 5 wherein $R^2$ is butyl.

7. A process of synthesizing a compound of formula III in accordance with claim 1 wherein the synthesis reaction is carried out at temperatures of from about 50° C. to about 150° C.

8. A process of synthesizing a compound of formula III in accordance with claim 1 wherein the synthesis reaction is carried out in the absence of a solvent.

9. A process of synthesizing a compound of formula III in accordance with claim 1 wherein the reaction is carried out in the presence of a solvent.

10. A process of synthesizing a compound of formula III in accordance with claim 9 wherein the solvent is xylene, toluene, hexane, butane, or heptane.

11. A process of synthesizing a compound of formula III in accordance with claim 1 wherein the synthesis reaction contains a proton source.

12. A process in accordance with claim 11 wherein the proton source is $C_{1-6}$ alcohol or water.

13. A process according to claim 12 wherein the alcohol is ethanol, methanol, butanol, propanol or isopropanol.

14. A process according to claim 12 wherein the ratio of water to tin halide is from about 0.10 to about 2.0 (mol/mol).

15. A process according to claim 12 wherein the ratio of alcohol to tin halide is from about 0.25 to about 1.0 (mol/mol).

16. A process of synthesizing a compound of formula III comprising:

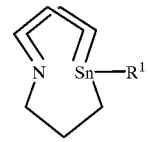

III stannylating a compound of formula I:

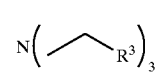

I wherein $R^3$ is a vinyl group or $CH_2CH_2X$ and X is a halogen, O-mesylate, O-tosylate or O-triflate;

with a stannylating agent to produce a compound of formula II:

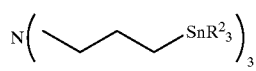

wherein $R^2$ is alkyl or aryl;

treating the compound of formula II in the presence of a proton source with a tin halide at temperatures of from about room temperature to about 200° C. to produce a compound of formula III.

17. A process of synthesizing a compound of formula III in accordance with claim 16 wherein $R^3$ is a vinyl group or $CH_2CH_2X$, and X is a halogen, O-mesylate, O-tosylate, or O-triflate.

18. A process of synthesizing a compound of formula III in accordance with claim 17 wherein $R^3$ is $CH_2CH_2X$ and X is chlorine.

19. A process of synthesizing a compound in accordance with claim 16 wherein $R^2$ is methyl, ethyl, propyl, butyl or phenyl.

20. A process of synthesizing a compound of formula III in accordance with claim 19 wherein $R^2$ is methyl, ethyl, propyl, or butyl.

21. A process of synthesizing a compound of formula III in accordance with claim 19 wherein $R^2$ is butyl.

22. A process of synthesizing a compound of formula III in accordance with claim 16 wherein the synthesis reaction is carried out at temperatures of from about 50° C. to about 150° C.

23. A process of synthesizing a compound of formula III in accordance with claim 16 wherein the synthesis reaction is carried out in the absence of a solvent.

24. A process of synthesizing a compound of formula III in accordance with claim 16 wherein the synthesis reaction is carried out in the presence of a solvent.

25. A process of synthesizing a compound of formula III in accordance with claim 24 wherein the solvent is xylene, toluene, hexane, ethane, or heptane.

26. A process of synthesizing a compound of formula III in accordance with claim 16 wherein the proton source is $C_{1-6}$ alcohol or water.

27. A process according to claim 26 wherein the alcohol is ethanol, methanol, butanol, propanol or isopropanol.

28. A process according to claim 26 wherein the ratio of water to tin halide is from about 0.10 to about 2.0 (mol/mol).

29. A process according to claim 26 wherein the ratio of alcohol to tin halide is from about 0.25 to about 1.0 (mol/mol).

30. A process of synthesizing a compound in accordance with claim 16 wherein the stannylating agent is $Bu_3SnLi$, $Bu_3SnK$, $Bu_3SnMgX$ or $Bu_3SnH$.

31. A process of synthesizing a compound in accordance with claim 30 wherein the stannylating agent is $Bu_3SnLi$ and $R^3=CH_2CH_2X$.

32. A process of synthesizing a compound in accordance with claim 16 wherein the tin halide is $SnCl_4$, $SnBr_4$, $SnI_4$.

33. A process of synthesizing a compound in accordance with claim 32 wherein the tin halide is $SnCl_4$.

34. A process of synthesizing a compound in accordance with claim 30 wherein the stannylating agent is $Bu_3SnH$ and $R^3$=vinyl.

* * * * *

UNITED STATES PATENT AND TRADEMARK OFFICE
CERTIFICATE OF CORRECTION

PATENT NO. : 6,069,265
DATED : August 19, 1999
INVENTOR(S) : Mark S. Jensen, Chunhua Yang, Nobuyoshi Yasuda, David A. Conlon and Yi Xiao It is certified that error appears in the above-identified patent and that said Letters Patent is hereby corrected as shown below:

Inventors: Mark S. Jensen, Holmdel; Chunhua Yang, Edison; Nobuyoshi Yasuda, Mountainside; David A. Conlon, Plainsboro; Yi Xiao, Fanwood, all of N.J.

Signed and Sealed this

Twenty-fifth Day of December, 2001

Attest:

Attesting Officer

JAMES E. ROGAN
Director of the United States Patent and Trademark Office